United States Patent [19]
Richard et al.

[11] Patent Number: 5,976,554
[45] Date of Patent: Nov. 2, 1999

[54] STERILIZING GAS COMPOSITIONS OF ETHYLENE OXIDE AND HEPTAFLUOROPROPANE

[75] Inventors: Robert G. Richard, Cheektowaga; Barbara R. Fellows-Decaire, West Amherst; Ian Robert Shankland, Williamsville; James Albert Batt, Depew, all of N.Y.

[73] Assignee: AlliedSignal Inc., Morristown, N.J.

[21] Appl. No.: 08/291,469

[22] Filed: Aug. 17, 1994

Related U.S. Application Data

[63] Continuation of application No. 07/880,809, May 8, 1992, abandoned.

[51] Int. Cl.[6] .............................. A61L 2/20; A61K 47/06; A61K 9/00
[52] U.S. Cl. ............................. 424/400; 422/34; 422/37; 252/372
[58] Field of Search ....................... 424/45, 400; 422/34, 422/37, 900; 252/170–172, 162, 364, 372, DIG. 9; 521/131, 910

[56] References Cited

U.S. PATENT DOCUMENTS

| | | | |
|---|---|---|---|
| 4,954,284 | 9/1990 | Batt et al. | 252/170 |
| 4,971,716 | 11/1990 | Batt et al. | 252/171 |
| 4,976,922 | 12/1990 | Chippett et al. | 422/34 |
| 5,039,484 | 8/1991 | Chippett et al. | 422/34 |
| 5,039,485 | 8/1991 | Conviser et al. | 422/34 |
| 5,118,494 | 6/1992 | Schultz et al. | 526/209 |
| 5,130,345 | 7/1992 | Li et al. | 521/131 |
| 5,162,385 | 11/1992 | Hartwig et al. | 521/129 |
| 5,169,873 | 12/1992 | Behme et al. | 521/114 |

*Primary Examiner*—Edward J. Webman
*Attorney, Agent, or Firm*—Jay P. Friedenson; Colleen D. Szuch

[57] ABSTRACT

The invention relates to compositions of ethylene oxide and heptafluoropropane and a method of sterilization using same. These environmentally acceptable compositions are chemically stable, minimally segregating, compatible with the objects being sterilized; provide sufficient vapor pressure to deliver the blend to the sterilization chamber, and possess improved flammability suppressant characteristics.

20 Claims, No Drawings

STERILIZING GAS COMPOSITIONS OF ETHYLENE OXIDE AND HEPTAFLUOROPROPANE

This application is a continuation, of application Ser. No. 07/880,809,filed May 8, 1992, now abandoned.

BACKGROUND OF THE INVENTION

Sterilization with a germicidal agent, such as ethylene oxide gas or ethylene oxide containing gas mixtures, has played an increasingly important role in sterilizing heat or moisture sensitive materials. Rapid growth in the use of sterile, disposable medical devices is just one consequence of gaseous sterilization with agents such as ethylene oxide. Gaseous sterilization of re-usable medical and surgical equipment using a non-flammable mixture of ethylene oxide and a carrier gas has also proven to be reliable, cost effective technology for many hospitals.

The basic gaseous sterilization process consists of evacuating the sterilization chamber containing articles to be sterilized, preconditioning the articles at an optimal relative humidity, generally between 20–70%, admitting the sterilizing gas at an appropriate pressure and temperature, maintaining contact between the sterilizing atmosphere and the articles to be sterilized for an appropriate time, and finally discharging and evacuating the chamber to remove the sterilant gas.

Although there are many variations on the basic process, the major factors which have to be controlled in order to effect the sterilization are exposure time, temperature, ethylene oxide pressure or partial pressure, and relative humidity.

By itself, ethylene oxide is an extremely flammable gas. Its flammability range extends from about 3.0% by volume to 100% by volume in air. Thus, when ethylene oxide is used alone as a sterilizing gas, precautions such as explosion proof equipment are mandatory.

A preferable practice is to blend the ethylene oxide with another fluid which serves to dilute the ethylene oxide and render the mixture as a whole, nonflammable. Two such blends which have been used as sterilizing gases are dichlorodifluoromethane (CFC-12)/ethylene oxide and carbon dioxide/ethylene oxide. Inert carrier gases like CFC-12 and carbon dioxide inhibit the flammability of ethylene oxide and provide sufficient autogenous vapor pressure to deliver the liquid mixture from the source cylinder to the heat exchanger of the sterilizer vessel where the liquid mixture is vaporized.

A disadvantage of using CFC-12 in sterilant gas mixtures is that fully halogenated chlorofluorocarbons such as CFC-12 have substantial potential for stratospheric ozone depletion and global warming.

Although the major purpose of the inert carrier gas component in these sterilizing gas mixtures is to mask the flammability characteristics of ethylene oxide, simple substitution of an arbitrary nonflammable gas does not necessarily ensure a useful sterilizing gas mixture. First, the flammability properties of the blend must be such that a sufficient amount of ethylene oxide (mg/liter at a typical pressure and temperature) is delivered by the blend to effect the sterilization in an appropriate time. The Association for the Advancement of Medical Instrumentation (AAMI) recommends an absolute minimum ethylene oxide concentration of 450 mg/liter. If the carrier gas does not mask the flammability to a sufficient extent, a lower concentration of ethylene oxide must be used to ensure nonflammability. In such a case either a longer exposure time is required to perform the sterilization, which affects productivity, or greater operating pressures are required to increase the effective ethylene oxide density in the sterilization chamber. Increasing the operating pressure is generally not a viable alternative because existing sterilization chambers may not be rated for the increased pressure, and as pointed out by Gunther in U.S. Pat. No. 3,589,861, increased pressure can lead to swelling and rupture of the sealed plastic bags commonly used to package disposable medical devices. Indeed, lower operating pressures are advantageous in this respect.

A candidate inert diluent or carrier gas must also be miscible with ethylene oxide in the liquid phase and must not segregate from the ethylene oxide to any great extent during vaporization. Segregation or fractionation can lead to potentially flammable or explosive situations. The degree of segregation that may occur during evaporation is related to the relative volatility of the components of the mixture.

Thus, the need exists for an environmentally acceptable carrier gas which is compatible with the objects being sterilized; chemically stable; minimally segregating; contains at least 27 mole percent ethylene oxide; and provides sufficient vapor pressure to deliver the liquid mixture to the sterilization chamber.

DESCRIPTION OF THE INVENTION

The invention relates to sterilizing gas compositions comprising effective amounts of ethylene oxide and heptafluoropropane and optionally a nonflammable, inert component which is more volatile than the ethylene oxide and heptafluoropropane blend and is other than pentafluoroethane. The primary function of the ethylene oxide is to effect sterilization while the primary function of heptafluoropropane is to mask the flammability of ethylene oxide. When these components are combined in effective amounts, an efficient, environmentally acceptable, minimally segregating, nonflammable sterilizing gas composition results.

Heptafluoropropane exists in two isomeric forms, 1,1,1,2,2,3,3-heptafluoropropane (HFC-227ca) and 1,1,1,2,3,3,3-heptafluoropropane (HFC-227ea). Each isomer possesses the desired properties of the invention hence, for purposes of this invention, heptafluoropropane will refer to either isomer or mixtures of the isomers in any proportions. Due to the close boiling points of HFC-227ca (−17.7° C.) and HFC-227ea (−18.7° C.), each of the above isomers when commercially produced may contain small amounts, perhaps up to 10 weight percent, of the other isomer. When a mixture of the isomers is used it may comprise: 10:90 weight percent HFC-227ca/HFC-227ea; or 10:90 weight percent HFC-227ea/HFC-227ca; or 25:75 weight percent HFC-227ca/HFC-227ea; or 25:75 weight percent HFC-227ea/HFC-227ca; or 50:50 weight percent HFC-227ca/HFC-227ea.

HFC-227ca is currently not commercially available. It may be synthesized however by following the procedure set forth in U.S. Pat. Nos. 2,404,374 and 2,490,764.

HFC-227ea may be purchased from Fluorochem, Ltd. of Derbyshur, United Kingdom. Alternately, it may be prepared by following the synthesis outlined in British Patent 902,590.

Since heptafluoropropane is not perhalogenated and does not contain chlorine, it is considered to be environmentally acceptable.

Preferably the heptafluoropropane/ethylene oxide compositions of the invention comprise from about 2 to about 11 weight percent ethylene oxide and from about 98 to about 89 weight percent heptafluoropropane.

In a more preferred embodiment, the compositions of the invention comprise from about 5 to about 9 weight percent ethylene oxide and from about 95 to about 91 weight percent heptafluoropropane.

In a still more preferred embodiment, the compositions of the invention comprise about 9 weight percent ethylene oxide and about 91 weight percent heptafluoropropane.

Both isomers of HFC-227 (and hence mixtures of the isomers) have sufficient vapor pressure to expel the ethylene oxide/HFC-227 mixture from the source cylinder to the sterilization chamber. Advantageously, the vapor pressure of each HFC-227 isomer is closer to the vapor pressure of ethylene oxide than CFC-12, further reducing the risk of segregation.

In another embodiment of the invention, a nonflammable, inert component which is more volatile than the HFC-227/ethylene oxide blend and which is not pentafluoroethane may be added to increase the vapor pressure of the HFC-227/ethylene oxide blend. Illustrative suitable components include chlorodifluoromethane (HCFC-22), 1,2,2,2-tetrafluoroethane (HFC-134a), 1,1,2,2-tetrafluoroethane (HFC-134), nitrogen, carbon dioxide, and sulfur hexafluoride. Other suitable volatile components will readily occur to those skilled in the art. Compositions incorporating these components comprise from about 2 to about 11 weight percent ethylene oxide, from about 10 to about 97 weight percent HFC-227, and from about 1 to about 88 weight percent of a more volatile, nonflammable, inert component other than pentafluoroethane.

In the process embodiment of the invention, the compositions comprising heptafluoropropane and ethylene oxide may be used as sterilizing gases in any manner well known in the art by essentially exposing the articles to be sterilized to the sterilizing gas under conditions and for a period of time necessary to achieve the desired degree of sterility. Typically, the process is effected by placing the articles to be sterilized in a chamber, evacuating the chamber, humidifying the chamber, and exposing the articles to the sterilizing gas for an appropriate period of time.

The heptafluoropropane employed in the following examples is essentially pure HFC-227ea, i.e., 99 weight percent HFC-227ea.

EXAMPLE 1

This example shows by means of vapor phase flammability measurements for various ethylene oxide/HFC-227ea gas mixtures in air, that HFC-227ea surprisingly suppresses the flammability of ethylene oxide to a greater extent than CFC-12.

Flammability measurements were performed using a method based on the ASTM E-681 method prescribed for measuring the flame limits of vapors in air. The ASTM E-681 method involves preparing a gas phase mixture of ethylene oxide, carrier gas, and air in a 5 liter spherical vessel. Once the components have been adequately mixed, the gas mixture is ignited at the center of the vessel. If a flame propagates away from the ignition source, then the gas mixture is deemed flammable. The extent of flame propagation necessary for the mixture to be classified as flammable is defined in the ASTM E-681 method definition.

Gas mixtures were prepared by evacuating the vessel and admitting HFC-227ea, ethylene oxide, and air and measuring the pressure after each addition. The composition of the blend is determined from the component partial pressures. A uniform composition was ensured by stirring the mixture with a magnetically driven propeller.

Two different ignition sources were employed to determine the flammability characteristics of the HFC-227ea/ethylene oxide blends. One ignition source consisted of a 45 Joule, 0.1 second duration electric spark discharged between two electrodes placed at the center of the vessel. The second ignition source consisted of a kitchen match head held in a coil of nichrome wire. Heating the wire electrically causes the match to ignite.

By preparing various compositions of ethylene oxide and HFC-227ea in air and determining their flammability, it was possible to map out the region of compositions in air which are flammable. See, e.g., P. A. Sanders, The Handbook of Aerosol Technology at 146 (2d ed. 1979). The maximum amount of ethylene oxide which can be blended with HFC-227ea, and remain nonflammable in all proportions in air, can be determined from such a plot. Table I summarizes the maximum or critical composition of ethylene oxide attainable with both CFC-12 and HFC-227ea.

TABLE I

| Carrier Gas | Maximum ethylene oxide composition (mole or volume percent) | Ignition Source |
| --- | --- | --- |
| HFC-227 ea | 25.8 | 45 J/0.1 sec spark |
| CFC-12 | 28.7 | 45 J/0.1 sec spark |
| HFC-227 ea | 32.3 | Heated wire/match |
| CFC-12 | 22.6 | Heated wire/match |

We note that when the spark ignition source is used that the data indicate that more ethylene oxide is attainable when CFC-12 rather than HFC-227ea is the carrier gas. The second ignition source utilized was the heated wire/match. It is known in the art that this ignition source is a much more rigorous flammability test. We therefore expected that the amount of ethylene oxide attainable with each carrier gas would decrease. The data show that when the heated wire/match is used that, in fact, the amount of ethylene oxide attainable in a nonflammable CFC-12 blend decreases over that reported with the spark ignition source. However, the data for HFC-227ea show that surprisingly the amount of ethylene oxide attainable with a nonflammable HFC-227ea blend increases. In fact, it increases dramatically. Up to 43% more ethylene oxide is provided for sterilization by using the HFC-227ea carrier gas, thus providing a more efficient sterilization process.

EXAMPLE 2

This example shows that nonflammable HFC-227ea/ethylene oxide blends unexpectedly contain more ethylene oxide than CFC-12 and pentafluoroethane (HFC-125).

Flammability measurements were performed for various fluorocarbon/ethylene oxide blends using the method outlined in Example 1 above. In this case only the heated wire/match ignition source was employed.

Flammability measurements were performed for blends of ethylene oxide with each of HFC-227ea, HFC-125, CFC-12, HFC-134a and HCFC-22. HFC-125, HFC-134a and HCFC-22 are also regarded as more environmentally acceptable fluorocarbons than CFC-12. HFC-125 has been identified as a replacement for CFC-12 in sterilant gas applications. HFC-134a has been suggested as an alternative for CFC-12 in certain air conditioning and refrigeration applications, and HCFC-22 is already produced commercially.

Table II lists the critical ethylene oxide concentration as well as some of the physical and molecular properties of the fluorocarbon diluents.

TABLE II

|  | CFC-12 | HFC-227 ea | HCFC-22 | HFC-134a | HFC-125 |
|---|---|---|---|---|---|
| Max. ethylene oxide (vol. %) | 22.6 | 32.3 | 11.3 | 12.8 | 23.7 |
| Halogen Content of Diluents |  |  |  |  |  |
| Wt. % Chlorine | 58.6 | 0.0 | 41.0 | 0.0 | 0.0 |
| Wt. % Fluorine | 31.4 | 78.1 | 44.0 | 74.5 | 79.2 |
| Wt. % Halogen | 90.0 | 78.1 | 85.0 | 74.5 | 79.2 |
| Mole % Chlorine | 40.0 | 0.0 | 20.0 | 0.0 | 0.0 |
| Mole % Fluorine | 40.0 | 53.8 | 40.0 | 50.0 | 62.5 |
| Mole % Halogen | 80.0 | 53.8 | 60.0 | 50.0 | 62.5 |

The data show that the flammability suppressant properties of these potential carrier gases do not follow the trend of halogen content. Based on hydrogen and halogen content, one would expect the following pattern of flammability suppressant behavior; CFC-12>HCFC-22>HFC-125>HFC-227ea>HFC-134a. However, the data listed in Table II show that HFC-227ea unexpectedly is the best flammability suppressant for ethylene oxide; the trend being HFC-227ea>HFC-125>CFC-12>HFC-134a>HCFC-22.

EXAMPLE 3

The vapor pressure of mixtures of ethylene oxide with each of HFC-227ea, HFC-227ca, a 10:90 weight percent mixture of HFC-227ca/HFC-227ea; a 10:90 weight percent mixture of HFC-227ea/HFC-227ca; a 25:75 weight percent mixture of HFC-227ca/HFC-227ea; a 25:75 weight percent mixture of HFC-227ea/HFC-227ca; and a 50:50 weight percent mixture of HFC-227ca/HFC-227ea are measured. The mixtures are prepared gravimetrically and allowed to reach thermal equilibrium in a temperature controlled water bath before determining the vapor pressure. A calibrated Bourdon gauge accurate to ±1% is used to measure the vapor pressures.

The results indicate that nonflammable blends of ethylene oxide and each of HFC-227ea, HFC-227ca, a 10:90 weight percent mixture of HFC-227ca/HFC-227ea; a 10:90 weight percent mixture of HFC-227ea/HFC-227ca; a 25:75 weight percent mixture of HFC-227ca/HFC-227ea; a 25:75 weight percent mixture of HFC-227ea/HFC-227ca; and a 50:50 weight percent mixture of HFC-227ca/HFC-227ea possess vapor pressures greater than 1 atmosphere which is sufficient to expel the liquid mixture from a source cylinder to the evacuated or partially evacuated sterilizer chamber.

EXAMPLE 4

This example shows that each of HFC-227ea, HFC-227ca, a 10:90 weight percent mixture of HFC-227ca/HFC-227ea; a 10:90 weight percent mixture of HFC-227ea/HFC-227ca; a 25:75 weight percent mixture of HFC-227ca/HFC-227ea; a 25:75 weight percent mixture of HFC-227ea/HFC-227ca; and a 50:50 weight percent mixture of HFC-227ca/HFC-227ea like CFC-12 are compatible with plastics and polymers commonly used in the construction of medical devices.

Compatibility tests are performed by exposing the test material listed in Table III to HFC-227ea fluorocarbon vapor at 24.7 psia and 130° F. for 16 hours. At the end of the exposure period any change in weight of the test material is determined and the test materials are visually inspected. The test is repeated for HFC-227ca, a 10:90 weight percent mixture of HFC-227ca/HFC-227ea; a 10:90 weight percent mixture of HFC-227ea/HFC-227ca; a 25:75 weight percent mixture of HFC-227ca/HFC-227ea; a 25:75 weight percent mixture of HFC-227ea/HFC-227ca; and a 50:50 weight percent mixture of HFC-227ca/HFC-227ea.

We observe essentially no change in the weight of the test material and that the test material is not physically harmed by the fluorocarbons. Based upon this, we conclude that each of HFC-227ea, HFC-227ca, a 10:90 weight percent mixture of HFC-227ca/HFC-227ea; a 10:90 weight percent mixture of HFC-227ea/HFC-227ca; a 25:75 weight percent mixture of HFC-227ca/HFC-227ea; a 25:75 weight percent mixture of HFC-227ea/HFC-227ca; and a 50:50 weight percent mixture of HFC-227ca/HFC-227ea are compatible with all of the test materials.

TABLE III

Polypropylene/Lexan
Polycarbonate/Lexan
Polystyrene
Polypropylene
Latex/Silicone Rubber
PVC
Cotton Gauze
Synthetic Skin

EXAMPLE 5–6

The flammability suppressant properties of HFC-227ca, a 10:90 weight percent mixture of HFC-227ca/HFC-227ea; a 10:90 weight percent mixture of HFC-227ea/HFC-227ca; a 25:75 weight percent mixture of HFC-227ca/HFC-227ea; a 25:75 weight percent mixture of HFC-227ea/HFC-227ca; and a 50:50 weight percent mixture of HFC-227ca/HFC-227ea are studied by repeating the experiment outlined in Example 1 above. The results obtained are substantially the same as those for HFC-227ea, i.e., HFC-227ea, a 10:90 weight percent mixture of HFC-227ca/HFC-227ea; a 10:90 weight percent mixture of HFC-227ea/HFC-227ca; a 25:75 weight percent mixture of HFC-227ca/HFC-227ea; a 25:75 weight percent mixture of HFC-227ea/HFC-227ca; and a 50:50 weight percent mixture of HFC-227ca/HFC-227ea each suppresses the flammability of ethylene oxide to a greater extent than CFC-12.

EXAMPLES 7–8

In accordance with Example 2, the ethylene oxide concentration is monitored for various blends of ethylene oxide with each of HFC-227ca, a 10:90 weight percent mixture of HFC-227ca/HFC-227ea; a 10:90 weight percent mixture of HFC-227ea/HFC-227ca; a 25:75 weight percent mixture of HFC-227ca/HFC-227ea; a 25:75 weight percent mixture of HFC-227ea/HFC-227ca; and a 50:50 weight percent mixture of HFC-227ca/HFC-227ea. The results obtained are substantially the same as those for HFC-227ea, i.e., nonflammable blends of ethylene oxide and each of HFC-227ca, a 10:90 weight percent mixture of HFC-227ca/HFC-227ea; a 10:90 weight percent mixture of HFC-227ea/HFC-227ca; a 25:75 weight percent mixture of HFC-227ca/HFC-227ea; a 25:75 weight percent mixture of HFC-227ea/HFC-227ca; and a 50:50 weight percent mixture of HFC-227ea/HFC-227ea unexpectedly contain more ethylene oxide than HFC-125/ethylene oxide and CFC-12/ethylene oxide blends.

What is claimed:

1. A nonflammable sterilant mixture comprising a sterilizing nonflammable effective amount of ethylene oxide and heptafluoropropane.

2. The mixture of claim 1 wherein said mixture comprises from about 89 to about 98 weight percent heptafluoropropane and from about 2 to about 11 weight percent ethylene oxide.

3. The mixture of claim 2 wherein said mixture comprises from about 91 to about 95 weight percent heptafluoropropane and from about 5 to about 9 weight percent ethylene oxide.

4. The mixture of claim 3 wherein said mixture comprises about 91 weight percent heptafluoropropane and about 9 weight percent ethylene oxide.

5. The mixture of claim 1 wherein said heptafluoropropane is 1,1,1,2,2,3,3-heptafluoropropane.

6. The mixture of claim 1 wherein said heptafluoropropane is 1,1,1,2,3,3,3-heptafluoropropane.

7. The mixture of claim 1 wherein said heptafluoropropane is a 90:10 combination of 1,1,1,2,2,3,3-heptafluoropropane and 1,1,1,2,3,3,3-heptafluoropropane, respectively.

8. The mixture of claim 1 wherein said heptafluoropropane is a 90:10 combination of 1,1,1,2,3,3,3-heptafluoropropane and 1,1,1,2,2,3,3-heptafluoropropane, respectively.

9. The mixture of claim 1 further comprising a nonflammable, inert component, said inert component being other than pentafluoroethane and being more volatile than the heptafluoropropane and ethylene oxide mixture to increase the vapor pressure of the mixture.

10. The mixture of claim 9 wherein the inert component is selected from the group consisting of chlorodifluoromethane, 1,2,2,2-tetrafluoroethane, 1,1,2,2-tetrafluoroethane, nitrogen, carbon dioxide, and sulfur hexafluoride.

11. The mixture of claim 9 wherein said mixture comprises from about 2 to about 11 weight percent ethylene oxide, from about 10 to about 97 weight percent heptafluoropropane, and from about 1 to about 88 weight percent of the inert component.

12. A method of sterilizing articles comprising exposing the articles to the mixture of claim 1 under conditions and for a period of time sufficient to sterilize the article.

13. A method of sterilizing articles comprising exposing the articles to the mixture of claim 2 under conditions and for a period of time sufficient to sterilize the article.

14. A method of sterilizing articles comprising exposing the articles to the mixture of claim 3 under conditions and for a period of time sufficient to sterilize the article.

15. A method of sterilizing articles comprising exposing the articles to the mixture of claim 4 under conditions and for a period of time sufficient to sterilize the article.

16. A method of sterilizing articles comprising exposing the articles to the mixture of claim 11 under conditions and for a period of time sufficient to sterilize the article.

17. A nonflammable sterilant mixture consisting essentially of a sterilizing nonflammable effective amount of ethylene oxide and heptafluoropropane.

18. A nonflammable sterilant mixture comprising a sterilizing effective amount of ethylene oxide and a nonflammable component in an amount effective to render the mixture nonflammable, said nonflammable component comprising heptafluoropropane.

19. The mixture of claim 18, wherein said nonflammable component further comprises an inert component to increase the vapor pressure of said mixture, said inert component being other than pentafluoroethane.

20. A method of sterilizing articles comprising exposing the articles to the mixture of claim 18 under conditions and for a period of time sufficient to sterilize the article.

* * * * *